US008932610B2

(12) United States Patent
Ruiz I Pol et al.

(10) Patent No.: US 8,932,610 B2
(45) Date of Patent: Jan. 13, 2015

(54) AQUEOUS CLEAR SOLUTIONS OF FLUOCINOLONE ACETONIDE FOR TREATMENT OF OTIC INFLAMMATION

(75) Inventors: Jaume Ruiz I Pol, Esplugues de Llobregat (ES); Francisca Izquierdo Torres, Esplugues de Llobregat (ES)

(73) Assignee: Laboratorios Salvat, S.A., Esplugues de Llobregat (Barcelona) (ES)

( * ) Notice: Subject to any disclaimer, the term of this patent is extended or adjusted under 35 U.S.C. 154(b) by 0 days.

(21) Appl. No.: 12/730,681

(22) Filed: Mar. 24, 2010

(65) Prior Publication Data

US 2011/0212932 A1    Sep. 1, 2011

(30) Foreign Application Priority Data

Mar. 1, 2010    (EP) .................................... 10155005

(51) Int. Cl.
| | | |
|---|---|---|
| *A61K 9/00* | (2006.01) | |
| *A61K 9/08* | (2006.01) | |
| *A61K 31/496* | (2006.01) | |
| *A61K 31/573* | (2006.01) | |
| *A61K 31/58* | (2006.01) | |
| *A61K 45/06* | (2006.01) | |

(52) U.S. Cl.
CPC .................. *A61K 9/0046* (2013.01); *A61K 9/08* (2013.01); *A61K 31/496* (2013.01); *A61K 31/573* (2013.01); *A61K 31/58* (2013.01); *A61K 45/06* (2013.01)
USPC ....................................................... 424/400

(58) Field of Classification Search
USPC ....................................................... 424/400
See application file for complete search history.

(56) References Cited

U.S. PATENT DOCUMENTS

| | | | | |
|---|---|---|---|---|
| 3,326,808 A | * | 6/1967 | Noseworthy | .................. 510/131 |
| 3,934,013 A | | 1/1976 | Poulsen | |
| 4,013,792 A | | 3/1977 | Eichman et al. | |
| 4,844,902 A | | 7/1989 | Grohe | |
| 5,786,363 A | | 7/1998 | Canovas Soler et al. | |
| 5,897,858 A | * | 4/1999 | Haslwanter et al. | ....... 424/78.04 |
| 5,990,100 A | * | 11/1999 | Rosenberg et al. | ........... 514/174 |
| 5,997,518 A | * | 12/1999 | Laibovitz et al. | ............. 604/296 |
| 6,235,722 B1 | * | 5/2001 | Jayapathy | ....................... 514/31 |
| 6,241,969 B1 | * | 6/2001 | Saidi et al. | ....................... 424/45 |
| 2001/0049366 A1 | | 12/2001 | Singh et al. | |
| 2003/0195179 A1 | * | 10/2003 | Sawa | ........................... 514/174 |
| 2004/0175383 A1 | * | 9/2004 | Barr et al. | ................... 424/146.1 |
| 2005/0244339 A1 | | 11/2005 | Jauernig et al. | |
| 2007/0253943 A1 | * | 11/2007 | Altunkaya | .................. 424/94.4 |
| 2009/0111780 A1 | | 4/2009 | Giordano | |
| 2009/0325938 A1 | | 12/2009 | Lichter et al. | |
| 2010/0036000 A1 | | 2/2010 | Lichter et al. | |

FOREIGN PATENT DOCUMENTS

| | | | |
|---|---|---|---|
| EP | 0995435 | A1 | 4/2000 |
| EP | 1312356 | A1 | 5/2003 |
| EP | 1321144 | B1 * | 6/2003 |
| GB | 1013180 | | 12/1965 |
| GB | 1013180 | A | 12/1965 |
| GB | 1133800 | | 11/1968 |
| GB | 1133800 | A | 11/1968 |
| GB | 1411432 | A | 10/1975 |
| JP | S51-110043 | | 9/1976 |
| JP | S50-132122 | A | 3/1977 |
| JP | S63-203629 | A | 8/1988 |
| JP | H11-500740 | T | 1/1999 |
| JP | 2003-510263 | T | 3/2003 |
| WO | 9001933 | A1 | 3/1990 |
| WO | 9639146 | A1 | 12/1996 |
| WO | 9956727 | A2 | 11/1999 |
| WO | 0122936 | A1 | 4/2001 |

OTHER PUBLICATIONS

Okonogi (AAPS PharmSciTech 2006; 7 (2)).*
Reid (Pharmaceutical Research, vol. 25, No. 11, Nov. 2008, pp. 2573-2580).*
Miller, D.D. et al., "Adrenocorticoids," Chapter 33, pp. 877-912, in "Foye's Principles of Medicinal Chemistry," Lemke, T.L. et al., eds., Wolters Kluwer 2007, 6th ed.
Coloe, J. et al., "Allergens in corticosteroid vehicles," Dermatitis, 2008, vol. 19(1), pp. 38-42.
Darbre, P.D. et al., "Paraben esters: review of recent studies of endocrine toxicity, absorption, esterase and human exposure, and discussion of potential human health risks," J Appl Toxicol. 2008, vol. 28(5), pp. 561-578.
Zimmer, K. et al., "Hydrocortisone delivery to healthy and inflamed eyes using a micellar polysorbate 80 solution or albumin nanoparticles," International Journal of Pharmaceutics, 1994, vol. 110, pp. 211-222.
European Search Report in European Patent Application No. 10155005.1, completed by the European Patent Office on Sep. 22, 2010.
Marsh, Roger R., et al., "Ototoxicity of antimycotics," Otolaryngology Head and Neck Surgery, 1989, pp. 134-136, vol. 100.
Morizono, T., et al., "Ototoxicity of ethanol in the tympanic cleft in animals," Acta Otolaryngology, 1981, pp. 33-40, vol. 92, Abstract Only.
Merchant, Sandra R., "Ototoxicity," Ear, Nose, and Throat, Veterinary Clinics of North America Small Animal Practive, 1994, pp. 971-980, vol. 24.

(Continued)

*Primary Examiner* — David J Blanchard
*Assistant Examiner* — Devang Thakor
(74) *Attorney, Agent, or Firm* — Tristan A. Fuierer; Moore & Van Allen, PLLC

(57) ABSTRACT

A pharmaceutical otic sterile preservative-free composition in the form of a clear aqueous solution comprising 0.01-0.10% (w/v) of Fluocinolone Acetonide, optionally accompanied by 0.1-0.8% of Ciprofloxacin or a pharmaceutically acceptable salt thereof, a nonionic surfactant, a tonicity adjusting agent and a viscosity increasing agent. It is useful for the prevention and/or treatment of otic inflammation, optionally accompanied by bacterial infection, and for administration from single-use containers.

12 Claims, No Drawings

(56) References Cited

OTHER PUBLICATIONS

Parker, F.L., et al., "The effect of various topical antibiotic and antibacterial agents on the middle and inner ear of the guinea-pig," J. Pharm. Pharmac, 1978, pp. 236-239, vol. 30.

Perez MD, Ronen., et al., "Vestibular and Cochlear Ototoxicity of Topical Antiseptics Assessed by Evoked Potentials," The Laryngoscope, 2000, pp. 1522-1527, vol. 110.

Japanese Office Action, Oct. 7, 2014.

Takashima, Yasuji, et al.; "Distribution of Fluocinolone Acetonide in Oil-in-Water Creams and Its Release from the Creams," Chem Pharm Bull, 1983, pp. 4040-4047, vol. 31.

* cited by examiner

AQUEOUS CLEAR SOLUTIONS OF FLUOCINOLONE ACETONIDE FOR TREATMENT OF OTIC INFLAMMATION

CROSS REFERENCE TO RELATED APPLICATIONS

This application claims priority under 35 U.S.C. §119(a) of European Patent Application No. EP10155005.1 for "Aqueous Clear Solutions of Fluocinolone Acetonide for Treatment of Otic Inflammation" filed on Mar. 1, 2010 in the name of Jaume RUIZ I POL, which is incorporated herein in its entirety.

FIELD

The present invention relates to compositions and methods comprising Fluocinolone Acetonide as anti-inflammatory active pharmaceutical ingredient, for the treatment of otic inflammation, optionally accompanied by bacterial infection.

BACKGROUND ART

Fluocinolone Acetonide is an anti-inflammatory corticosteroid successfully used for topical treatment of otic inflammation. It is known in combination with an antibacterial and an antiseptic for treatment of external or middle ear infections (cf. e.g. US 20090111780 A1).

Fluocinolone Acetonide (a 6,9-difluoro-16,17-acetonide corticosteroid) is classified as high to medium potency anti-inflammatory agent depending on the concentration and the vehicle used. The 9-F group increases glucocorticoid activity and prevents metabolic oxidation of the 11-OH group (cf. e.g. T. L. Lemke and D. A. Williams, "Foye's Principles of Medicinal Chemistry", Wolters Kluwer 2007, 6th ed., p. 902).

Fluocinolone Acetonide is virtually insoluble in water. It is actually more insoluble than other corticosteroids (e.g. Dexamethasone or Hydrocortisone) that are also used for similar purposes. The acetonide (ketal) moiety at the 16,17-position of fluocinolone provides potency as topical anti-inflammatory agent as it enhances lipophilicity (ibid, p. 895), but consequently reduces solubility. In fact, otic drops containing Fluocinolone Acetonide are organic solutions (e.g. otic oil drops commercialized by Hill Dermaceuticals) or aqueous-organic suspensions (e.g. the aqueous suspension preparations described in EP 1312356 A1). Otic drops containing Fluocinolone Acetonide and Ciprofloxacin are on the market in the form of aqueous-organic composition containing preservatives and less than 75% of water (e.g. otic drops commercialized by Salvat in Spain for treatment of external otitis).

Examples of disorders that entail otic inflammation are eczematoid external otitis, keloids, granular myringitis, bullous myringitis or sudden deafness. Examples of disorders that entail otic inflammation accompanied by bacterial infection are diffuse external otitis (swimmers's ear), localized external otitis (forunculosis), traumatic tympanic membrane perforations, herpes zoster oticus (Ramsay Hunt syndrome), otitis media with effusión (OME, also called serous or secretory otitis media (SOM) or glue ear), otorrhea through tympanostomy tubes, acute otitis media with tympanostomy tubes (AOMT), acute otitis media (AOM) or chronic suppurative otitis media (CSOM).

In some cases, the presence in otic drops of solvents different from water and/or preservatives entails some adverse effects, such as allergic responses or irritation (cf. e.g. J. Coloe and M. J. Zirwas, "Allergens in corticosteroid vehicles", *Dermatitis* 2008, vol. 19(1), pp. 38-42). Also, some concerns about the suitability of using preservatives such as parabens for topical application have been raised due to their potential toxicity (cf. e.g. P. D. Darbre and P. W. Harvey, "Paraben esters: review of recent studies of endocrine toxicity, absorption, esterase and human exposure, and discussion of potential human health risks", *J Appl Toxicol.* 2008, vol. 28(5), pp. 561-578). Thus, it is highly desirable to provide improved pharmaceutical compositions with vehicles of higher water content for treatment of otic inflammation, especially in cases where it is accompanied by bacterial infection.

SUMMARY OF THE INVENTION

The present invention provides a pharmaceutical otic sterile preservative-free composition in the form of a clear aqueous solution of Fluocinolone Acetonide that comprises more than 90% water (all percentages are w/v), and which is suitable for administration as drops from a single-dose container (obviously, although not specially preferred, administration from a multi-dose container would also be possible).

Dropping an otic liquid pharmaceutical composition from single-dose containers has many advantages. For example, it permits the administration of a precise dose of the composition. Another advantage is that, since a new container is open each time, the administered composition is always sterile, thus avoiding the possibility of contamination by microorganisms or by body secretions. Besides the advantage of greater hygiene, the single-dose container is also more pleasant to use and manipulate than multi-dose containers.

However, to be suitable for dropping from sterile single-dose containers, an otic composition must fulfill several requirements, which appeared to be difficult in the case of a highly insoluble active pharmaceutical ingredient, such as Fluocinolone Acetonide. If, as customary, sterilization is to be done by filtration through a 0.22 μm filter, the composition must be a clear solution, i.e. substantially free from particles in suspension. Besides, it is highly desirable that the solution is free from preservatives, such as methylparaben and propylparaben.

Inventors have found that it is appropriate to use a total amount of 0.5-4.0% of one or more nonionic surfactants with a hydrophilic-lipophilic balance (HLB) value between 14 and 18 to obtain a pharmaceutical otic sterile preservative-free composition in the form of a clear aqueous solution (i.e. substantially free from particles in suspension) of 0.01-0.10% of Fluocinolone Acetonide. In this composition, a total amount of 0.5-4.0% of one or more tonicity adjusting agents is appropriate for adjusting tonicity, and a total amount of 0.05-1.00% of one or more viscosity increasing agents is appropriate for adjusting viscosity. The composition can optionally comprise an amount of one or more pH adjusting agents to adjust pH between 4.0 and 5.0. These excipients, in the mentioned amounts, also provide a pharmaceutical otic sterile preservative-free composition in the form of a clear aqueous solution in the case that Fluocinolone Acetonide is accompanied by 0.1-0.8% of Ciprofloxacin or a pharmaceutically acceptable salt thereof, this composition being useful when otic inflammation is accompanied by bacterial infection.

The pharmaceutical composition of the present invention shows a number of advantages. It is a clear aqueous solution substantially free from solid particles in suspension that can be sterilized by filtration without loss of active ingredient, which entails good dose reproducibility. It shows also good stability. This allows having a sterile preservative-free composition that can be contained in disposable single-dose containers for topical use in drop form. Also, lack of preservatives and of non-aqueous solvents avoids the possible adverse effects that might cause these compounds.

Pharmaceutically acceptable examples of nonionic surfactants with a HLB value between 14 and 18 include, but are not limited to sorbitan polyoxyethylene fatty acid derivatives; polyoxyethylene hydrogenated castor oil derivatives; polyoxyethylene fatty acid derivatives, polyoxyethylene-polyoxypropylene co-polymers and block-co-polymers.

In an embodiment of the present invention the pharmaceutically acceptable examples of nonionic surfactants with a HLB value between 14 and 18 are selected from the group consisting of sorbitan polyoxyethylene fatty acid derivatives such as Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate) and Polysorbate 80 (polyoxyethylene (20) sorbitan monooleate); polyoxyethylene hydrogenated castor oil derivatives such as polyoxyethylene (60) hydrogenated castor oil, polyoxyethylene glycol (60) hydrogenated castor oil and polyoxyethylene glycol (40) hydrogenated castor oil; polyoxyethylene fatty acid derivatives such as polyoxyethylene (20) stearate, polyoxyethylene (32) distearate, polyoxyethylene (20) oleate, polyoxyethylene (32) oleate and polyoxyethylene (32) dioleate; fatty alcohol ethoxylates such as polyoxyethylene (20) oleyl alcohol, polyoxyethylene (20) stearyl alcohol and polyoxyethylene (20) cetearyl alcohol, polyoxyethylene-polyoxypropylene co-polymers and block-co-polymers. In a preferred embodiment the nonionic surfactant is Polysorbate 80.

In another embodiment of the present invention the pharmaceutically acceptable tonicity adjuster agents are selected from the group consisting of dextrose, glycerin, sorbitol, mannitol, xylitol, polyethylene glycol, propylene glycol, dextran or electrolytes such as potassium chloride, sodium chloride, calcium chloride, sodium phosphate, potassium phosphate, sodium bicarbonate, calcium carbonate and sodium lactate. In a preferred embodiment the tonicity adjuster agent is glycerin.

In still another embodiment of the present invention the pharmaceutically acceptable viscosity increasing agents are selected from the group consisting of polyvinylpirrolidone, such as Povidone K 25, Povidone K 30 and Povidone K 90F; polyvinyl alcohol, xanthan gum, guar gum, welan gum, tragacanth gum, ceratonia gum, agar, methylcellulose, ethylcellulose, hydroxyethyl cellulose, hydroxyethylmethyl cellulose, hydroxypropyl cellulose, sodium carboxymethylcellulose, calcium carboxymethylcellulose, polyethylene glycol, glycerin, carrageenan, sodium alginate, potassium alginate, propylene glycol alginate, sodium hyaluronate, carbomers and maltodextrin. In a preferred embodiment the viscosity increasing agent is a polyvinylpirrolidone selected from Povidone K 25, Povidone K 30 and Povidone K 90F. In a particularly preferred embodiment the viscosity increasing agent is Povidone K 90F.

Optionally, appropriate pH adjusting agents can be added, as solids or as aqueous solutions. Pharmaceutically acceptable examples of pH adjusting agents include, but are not limited to, citric acid and salts thereof; tartaric acid and salts thereof, phosphoric acid and salts thereof, carbonic acid and salts thereof, lactic acid and salts thereof, acetic acid and salts thereof, sulphuric acid and salts thereof, boric acid and salts thereof, maleic acid and salts thereof, succinic acid and salts thereof; hydrochloric acid, nitric acid, sodium hydroxide, potassium hydroxide, triethanolamine, diisopropanolamine or mixtures thereof.

In another embodiment of the present invention the pharmaceutically acceptable pH adjusting agents are selected from the group consisting of citric acid and salts thereof, such as sodium citrate, potassium citrate, calcium citrate and lithium citrate; tartaric acid and salts thereof, such as sodium tartrate, potassium tartrate, calcium tartrate and lithium tartrate; phosphoric acid and salts thereof, such as sodium dihydrogenphosphate and sodium monohydrogenphosphate, lithium phosphate, potassium phosphate and calcium phosphate; carbonic acid and salts thereof, such as sodium carbonate and sodium hydrogencarbonate; lactic acid and salts thereof, such as sodium lactate, potassium lactate and calcium lactate; acetic acid and salts thereof, such as sodium acetate, potassium acetate and calcium acetate; sulphuric acid and salts thereof, such as sodium sulphate and potassium sulphate; boric acid and salts thereof, such as sodium borate; maleic acid and salts thereof, such as lithium maleate, sodium maleate, potassium maleate and calcium maleate; succinic acid and salts thereof, such as lithium succinate, sodium succinate, potassium succinate and calcium succinate; hydrochloric acid, nitric acid, sodium hydroxide, potassium hydroxide, triethanolamine, diisopropanolamine or mixtures thereof.

In a preferred embodiment, the pharmaceutical composition comprises the following ingredients: 0.02-0.03% of Fluocinolone Acetonide, optionally accompanied by 0.2-0.4% of Ciprofloxacin or a pharmaceutically acceptable salt thereof; 2-3% of Polysorbate 80; 2-3% of glycerin; 0.1-0.3% of Povidone K 90F; optionally, an amount of one or more pharmaceutically acceptable pH adjusting agent q.s. to adjust pH 4.0-5.0; and water In a preferred embodiment the composition consist exclusively of the above mentioned ingredients.

In a particularly preferred embodiment, the pharmaceutical composition has the following composition: 0.025% of Fluocinolone Acetonide; 2.5% of Polysorbate 80; 2.4% of glycerin; 0.2% of Povidone K 90F; sodium lactate q.s. to adjust pH 4.0-5.0 and water.

In a particularly preferred embodiment, the pharmaceutical composition has the following composition: 0.025% of Fluocinolone Acetonide, 0.349% of ciprofloxacin HCl; 2.5% of Polysorbate 80; 2.4% of glycerin; 0.2% of Povidone K 90F; and water.

In a preferred embodiment, the pharmaceutical composition is sterilized and contained in disposable single-dose containers for topical use in drop form. Another aspect of the invention relates to a method for the prevention and/or treatment of an individual suffering from otic inflammation, optionally accompanied by bacterial infection, comprising the topical administration to the individual of a therapeutically effective amount of the pharmaceutical composition as described above.

In particular, the otic inflammation is eczematoid external otitis, keloids, granular myringitis, bullous myringitis or sudden deafness.

In particular, the otic inflammation accompanied by bacterial infection is diffuse external otitis (swimmers's ear), localized external otitis (forunculosis), traumatic tympanic membrane perforations, herpes zoster oticus (Ramsay Hunt syndrome), otitis media with effusión (OME, also called glue ear), otorrhea through tympanostomy tubes, acute otitis media with tympanostomy tubes (AOMT), acute otitis media (AOM) or chronic suppurative otitis media (CSOM).

Another aspect of the invention refers to a pharmaceutical composition as described above for its use as a medicament. In particular, its use is for the prevention and/or treatment of otic inflammation, optionally accompanied by bacterial infection.

Another aspect of the invention is the use of the pharmaceutical composition as described above for the preparation of a medicament for the prevention and/or treatment of otic inflammation, optionally accompanied by bacterial infection.

Another aspect of the invention is a method for the prevention and/or treatment of an individual suffering from otic inflammation, optionally accompanied by bacterial infection, comprising the topical administration to the individual of a therapeutically effective amount of a pharmaceutical composition described above.

In one embodiment the otic inflammation is eczematoid external otitis, keloids, granular myringitis, bullous myringitis or sudden deafness.

In another embodiment the otic inflammation accompanied by bacterial infection is diffuse external otitis, localized external otitis, traumatic tympanic membrane perforations, herpes zoster oticus, otitis media with effusion, otorrhea through tympanostomy tubes, acute otitis media with tympanostomy tubes, acute otitis media or chronic suppurative otitis media.

Throughout the description and claims the term "comprise" and variations of the word, such as "comprising", is not intended to exclude other technical features, additives or components.

Additional objects, advantages and features of the invention will become apparent to those skilled in the art upon examination of the description or may be learned by practice of the invention.

EXAMPLES

The following examples are provided by way of illustration, and are not intended to be limiting of the present invention.

Example 1

Aqueous Solution Comprising Fluocinolone

| Ingredients | Amount (w/v) |
| --- | --- |
| Fluocinolone Acetonide | 0.025% |
| Polysorbate 80 | 2.500% |
| Povidone K 90 F | 0.200% |
| Glycerin | 2.400% |
| Lactic acid/NaOH | q.s. to adjust pH 4.0-5.0 |
| Water | q.s. to 100% |

Example 2

Aqueous Solution Comprising Fluocinolone+Ciprofloxacin

| Ingredients | Amount |
| --- | --- |
| Fluocinolone Acetonide | 0.025% |
| Ciprofloxacin HCl | 0.349% |
| Polysorbate 80 | 2.500% |
| Povidone K 90 F | 0.200% |
| Glycerin | 2.400% |
| Water | q.s. to 100% |

Example 3

Aqueous Solution Comprising Fluocinolone

| Ingredients | Amount |
| --- | --- |
| Fluocinolone Acetonide | 0.025% |
| PEG-60 hydrogenated castor oil | 2.500% |
| Povidone K 90 F | 0.200% |
| Glycerin | 2.400% |
| Lactic acid/NaOH | q.s. to adjust pH 4.0-5.0 |
| Water | q.s. to 100% |

Example 4

Aqueous Solution Comprising Fluocinolone+Ciprofloxacin

| Ingredients | Amount |
| --- | --- |
| Fluocinolone Acetonide | 0.025% |
| Ciprofloxacin HCl | 0.349% |
| Polysorbate 20 | 2.500% |
| Sodium carboxymethylcellulose | 0.500% |
| Glycerin | 2.400% |
| Lactic acid/NaOH | q.s. to adjust pH 4.0-5.0 |
| Water | q.s. to 100% |

Example 5

Aqueous Solution Comprising Fluocinolone

| Ingredients | Amount |
| --- | --- |
| Fluocinolone Acetonide | 0.025% |
| Ceteareth-20 | 2.500% |
| Povidone K 90 F | 0.200% |
| Glycerin | 1.000% |
| Sodium chloride | 0.500% |
| Lactic acid/NaOH | q.s. to adjust pH 4.0-5.0 |
| Water | q.s. to 100% |

Example 6

Absence of Solid Particles in Suspension

Concentrations of active ingredient in two batches of a pharmaceutical composition comprising Fluocinolone Acetonide and Ciprofloxacin were measured before and after filtration to confirm the absence of active particles in suspension that could be retained in the 0.22 μm filter leading to a loss of active ingredient.

| | Batch 1 | | | |
| --- | --- | --- | --- | --- |
| | Before filtration | | After filtration | |
| Active ingredient | Concentration | % of theoretical | Concentration | % of theoretical |
| Ciprofloxacin HCl | 0.342% | 98.0% | 0.341% | 97.7% |

-continued

Batch 1

| | Before filtration | | After filtration | |
|---|---|---|---|---|
| Active ingredient | Concentration | % of theoretical | Concentration | % of theoretical |
| Fluocinolone Acetonide | 0.025% | 100.0% | 0.025% | 100.0% |

Batch 2

| | Before filtration | | After filtration | |
|---|---|---|---|---|
| Active ingredient | Concentration | % of theoretical | Concentration | % of theoretical |
| Ciprofloxacin HCl | 0.342% | 98.0% | 0.342% | 98.0% |
| Fluocinolone Acetonide | 0.025% | 100.0% | 0.025% | 100.0% |

Example 7

Absence of Solid Particles in Suspension

Dynamic light scattering determinations of a pharmaceutical composition comprising Fluocinolone Acetonide and ciprofloxacin were carried out before and after filtration to confirm the absence of active particles in suspension that could be retained in the 0.22 µm filter leading to a loss of active ingredient.

| Before filtration | | After filtration | |
|---|---|---|---|
| ZAve (nm) | Poly. Index | ZAve (nm) | Poly. Index |
| 11.933 | 0.177 | 11.326 | 0.184 |

Example 8

Absence of Solid Particles in Suspension

Dynamic light scattering determinations of a pharmaceutical composition comprising Fluocinolone Acetonide were carried out before filtration to confirm the absence of active particles in suspension that could be retained in the 0.22 µm filter leading to a loss of active ingredient.

| Before filtration | |
|---|---|
| ZAve (nm) | Poly. Index |
| 9.276 | 0.152 |

The invention claimed is:

1. A pharmaceutical otic sterile preservative-free composition in the form of a clear aqueous solution comprising the following ingredients, in w/v percentages:
   (i) 0.01-0.10% of Fluocinolone Acetonide, optionally accompanied by 0.1-0.8% of Ciprofloxacin or a pharmaceutically acceptable salt thereof;
   (ii) a total of 0.5-4.0% of Polysorbate 80;
   (iii) a total of 0.5-4.0% of one or more pharmaceutically acceptable tonicity adjusting agents;
   (iv) a total of 0.05-1.00% of one or more pharmaceutically acceptable viscosity increasing agents;
   (v) optionally, an amount of one or more pharmaceutically acceptable pH adjusting agents in q.s. to adjust pH 4.0-5.0; and
   (vi) more than 90% water;
   wherein the composition is substantially free from particles in suspension and lacks non-aqueous solvents.

2. The pharmaceutical composition according to claim 1, wherein the one or more pharmaceutically acceptable tonicity adjusting agents is selected from the group consisting of dextrose, glycerin, sorbitol, mannitol, xylitol, polyethylene glycol, propylene glycol, dextran, potassium chloride, sodium chloride, calcium chloride, sodium phosphate, potassium phosphate, sodium bicarbonate, calcium carbonate, sodium lactate, and mixtures thereof.

3. The pharmaceutical composition according to claim 2, wherein the pharmaceutically acceptable tonicity adjusting agent is glycerin.

4. The pharmaceutical composition according to claim 1, wherein the one or more pharmaceutically acceptable viscosity increasing agents is selected from the group consisting of polyvinylpyrrolidone, polyvinyl alcohol, xanthan gum, guar gum, welan gum, tragacanth gum, ceratonia gum, agar, methylcellulose, ethyl cellulose, hydroxyethyl cellulose, hydroxyethylmethyl cellulose, hydroxypropyl cellulose, sodium carboxymethylcellulose, calcium carboxymethylcellulose, polyethylene glycol, glycerin, carrageenan, sodium alginate, potassium alginate, propylene glycol alginate, sodium hyaluronate, carbomers, maltodextrin, and mixtures thereof.

5. The pharmaceutical composition according to claim 4, wherein the one or more pharmaceutically acceptable viscosity increasing agent is a polyvinylpyrrolidone selected from the group consisting of Povidone K 25, Povidone K 30, Povidone K 90F, and mixtures thereof.

6. The pharmaceutical composition according to claim 5, wherein the pharmaceutically acceptable viscosity increasing agent is Povidone K 90F.

7. The pharmaceutical composition according to claim 1, comprising one or more pharmaceutically acceptable pH adjusting agents, wherein the one or more pharmaceutically acceptable pH adjusting agent is selected from the group consisting of citric acid, sodium citrate, potassium citrate, calcium citrate, lithium citrate, tartaric acid, sodium tartrate, potassium tartrate, calcium tartrate, lithium tartrate, phosphoric acid, sodium dihydrogenphosphate, sodium monohydrogenphosphate, lithium phosphate, potassium phosphate, calcium phosphate, sodium carbonate, sodium hydrogencarbonate, lactic acid, sodium lactate, potassium lactate, calcium lactate, acetic acid, sodium acetate, potassium acetate, calcium acetate, sulphuric acid, sodium sulphate, potassium sulphate, boric acid, sodium borate, maleic acid, lithium maleate, sodium maleate, potassium maleate, calcium maleate, succinic acid, lithium succinate, sodium succinate, potassium succinate, calcium succinate, hydrochloric acid, nitric acid, sodium hydroxide, potassium hydroxide, triethanolamine, diisopropanolamine, and mixtures thereof.

8. The pharmaceutical composition according to claim 1, wherein the w/v percentages are as follows:
   (i) 0.02-0.03% of Fluocinolone Acetonide, optionally accompanied by 0.2-0.4% of Ciprofloxacin or a pharmaceutically acceptable salt thereof;
   (ii) 2-3% of Polysorbate 80;
   (iii) 2-3% of glycerin;

(iv) 0.1-0.3% of Povidone K 90F;
(v) optionally, an amount of one or more pharmaceutically acceptable pH adjusting agents in q.s. to adjust pH 4.0-5.0; and
(vi) more than 90% water.

9. The pharmaceutical composition according to claim 1, wherein the pharmaceutical composition is sterilized and contained in disposable single-dose containers for topical use in drop form.

10. A method for the prevention and/or treatment of otic inflammation, optionally accompanied by bacterial infection, in an individual, comprising the topical administration to the individual of a therapeutically effective amount of the pharmaceutical composition of claim 1.

11. The method according to claim 10, wherein the otic inflammation is eczematoid external otitis, keloids, granular myringitis, bullous myringitis or sudden deafness.

12. The method according to claim 10, wherein the otic inflammation accompanied by bacterial infection is diffuse external otitis, localized external otitis, traumatic tympanic membrane perforations, herpes zoster oticus, otitis media with effusion, otorrhea through tympanostomy tubes, acute otitis media with tympanostomy tubes, acute otitis media or chronic suppurative otitis media.

* * * * *